United States Patent [19]

Turowski et al.

[11] Patent Number: 5,071,960

[45] Date of Patent: Dec. 10, 1991

[54] HIGH MOLECULAR WEIGHT PROTEIN/FATTY ACID CONDENSATION PRODUCTS WHICH ARE VERY WELL TOLERATED BY THE SKIN AND MUCOSA

[75] Inventors: Angelika Turowski, Eberbach; Jochen M. Quack, Eppstein/Tanus; Alwin Reng, Kelkheim; Arno Holst, Wiesbaden, all of Fed. Rep. of Germany

[73] Assignees: Hoechst Aktiengesellschaft, Frankfurt am Main; Deutsche Gelatine-Fabriken Stoess AG, Eberbach/Baden, both of Fed. Rep. of Germany

[21] Appl. No.: 578,341

[22] Filed: Sep. 6, 1990

[30] Foreign Application Priority Data

Sep. 7, 1989 [DE] Fed. Rep. of Germany ....... 3929740

[51] Int. Cl.$^5$ .................. C07k 15/20; C08H 1/06; C08H 5/02; C08H 5/04

[52] U.S. Cl. .................................. 530/356; 252/89.1; 252/132; 252/174.23; 252/315.1; 252/356; 252/DIG. 5; 252/DIG. 13; 252/DIG. 14; 435/68.1; 530/362; 530/363; 530/377; 530/378; 530/354; 530/357; 530/360; 530/407

[58] Field of Search ............... 530/362, 363, 354, 356, 530/357, 407, 377, 378, 360, 353; 405/68.1; 252/356, 315.1, 174.23, 132, 89.1, DIG. 5, DIG. 13, DIG. 14

[56] References Cited

U.S. PATENT DOCUMENTS

| | | | |
|---|---|---|---|
| 2,015,912 | 10/1935 | Sommer | 530/362 |
| 2,100,090 | 11/1937 | Sommer et al. | 530/362 X |
| 2,113,819 | 4/1938 | Tucker | 530/354 |
| 2,119,872 | 6/1938 | Wiegand | 530/362 |
| 2,121,305 | 6/1938 | Schrader et al. | 530/363 X |
| 2,127,841 | 8/1938 | Gellendien | 530/363 |
| 2,151,241 | 3/1939 | Sommer et al. | 530/362 |
| 2,728,759 | 12/1955 | Keil | 530/356 X |
| 3,004,021 | 10/1961 | Selle et al. | 530/357 |
| 3,738,913 | 6/1973 | Johnsen et al. | 435/68.1 |
| 3,898,129 | 8/1975 | Fujimoto et al. | 530/356 |
| 3,985,722 | 10/1976 | Yoshida et al. | 530/360 |
| 4,067,963 | 1/1978 | Ishii | 530/363 |
| 4,234,475 | 11/1980 | Sokol | 530/357 |
| 4,279,996 | 7/1981 | Yoshioka et al. | 435/68.1 |
| 4,285,986 | 8/1981 | Cioca et al. | 530/356 X |
| 4,293,647 | 10/1981 | Monsheimer et al. | 435/68.4 |
| 4,324,805 | 4/1982 | Olsen | 435/68.1 |
| 4,406,833 | 9/1983 | Boehme et al. | 530/356 |
| 4,451,385 | 5/1984 | Tavss et al. | 530/356 X |
| 4,494,994 | 1/1985 | Cioca et al. | 530/356 X |
| 4,659,740 | 4/1987 | Usher | 530/353 |
| 4,705,682 | 10/1987 | Moeller et al. | 530/356 X |

OTHER PUBLICATIONS

Kirk-Othmeri Encyclopedia of Chemical Technology, vol. 19, 1969, pp. 508-516.

Primary Examiner—Howard E. Schain

[57] ABSTRACT

High molecular weight protein/fatty acid condensation products obtained by reaction of one mole of a protein hydrolysate of average molecular mass 3,000 to 7,000 with 0.5 to 3, preferably 2 to 2.5, moles of a $C_{12}$-$C_{18}$-fatty acid chloride in aqueous medium at a pH of 7 to 12. These protein/fatty acid condensation products are distinguished by eliciting no mucosal irritation whatever. They are therefore outstandingly suitable as surfactants for mild washing and cleansing agents.

7 Claims, 7 Drawing Sheets

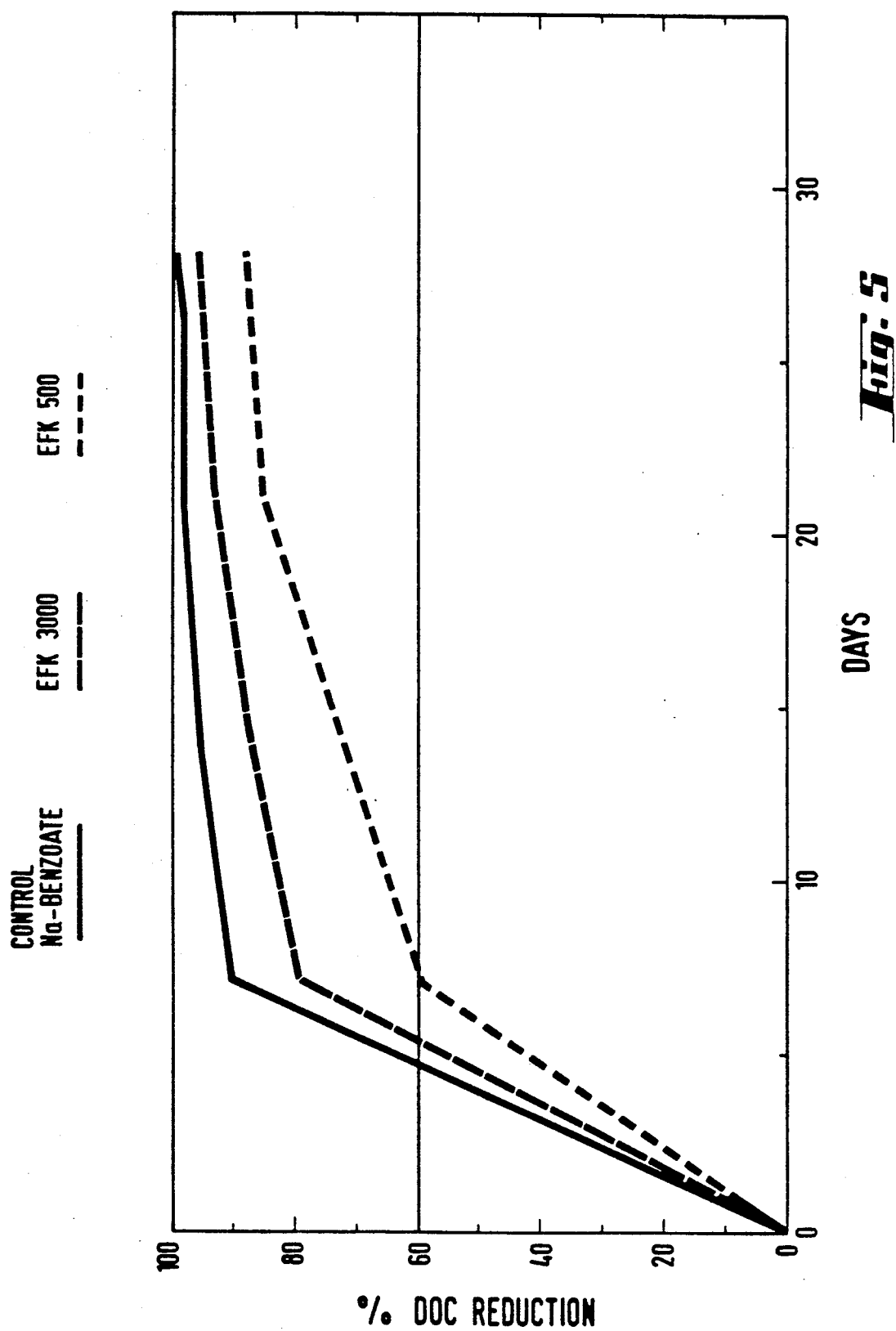

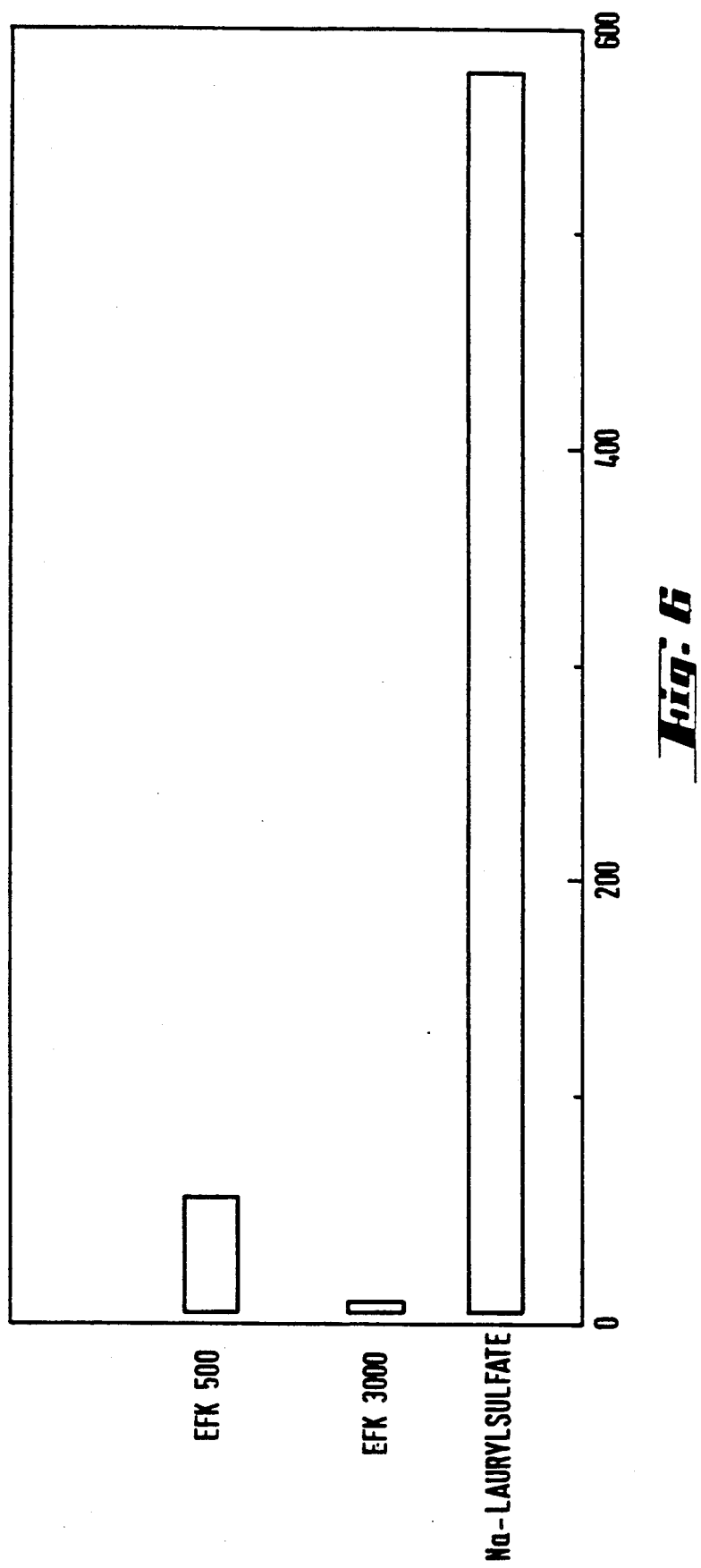

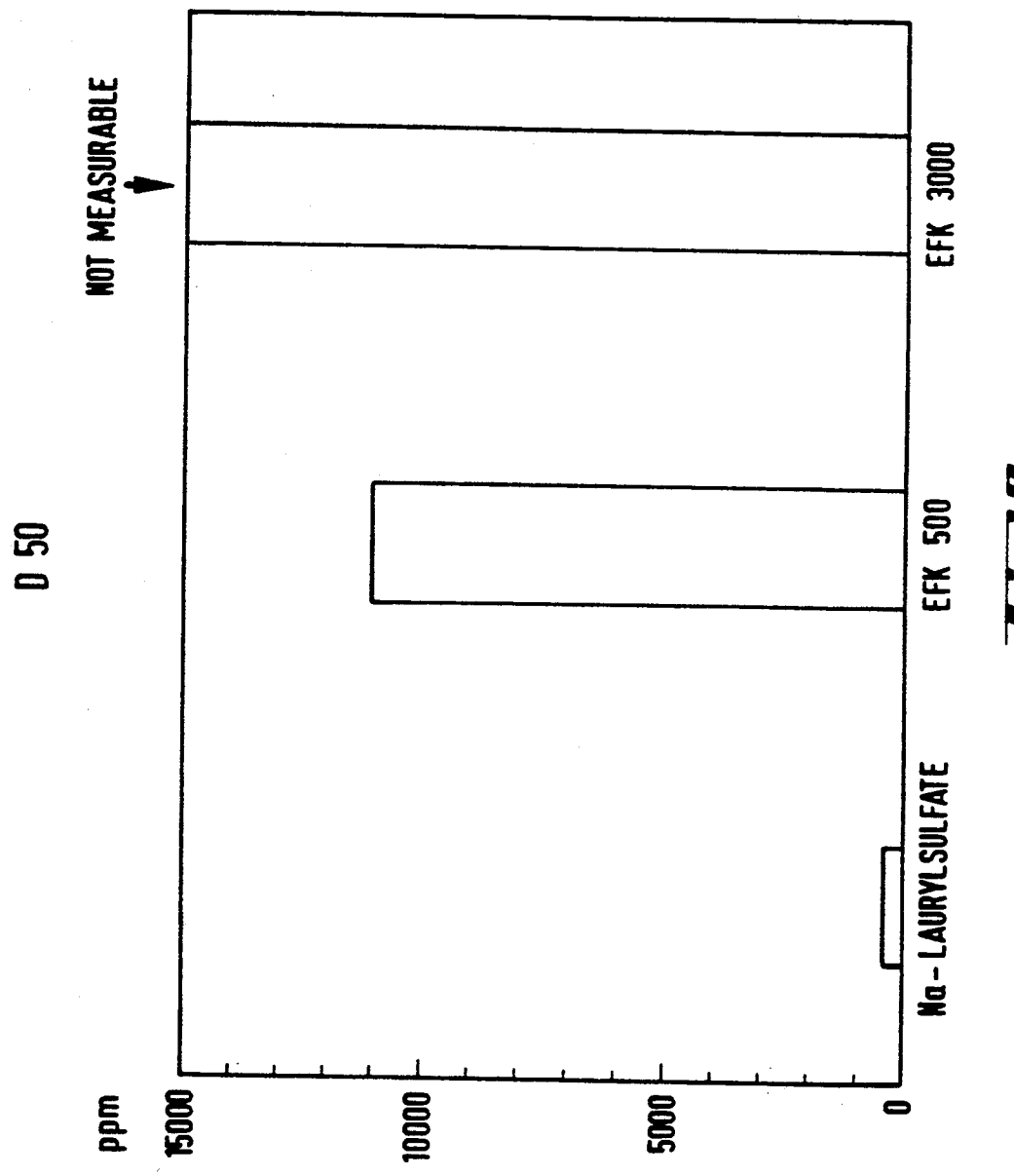

HIGH MOLECULAR WEIGHT PROTEIN/FATTY ACID CONDENSATION PRODUCTS WHICH ARE VERY WELL TOLERATED BY THE SKIN AND MUCOSA

DESCRIPTION

In recent years there has been a worldwide trend towards the development, in the design of cosmetic washing and cleansing agents such as shampoos, bath additives, wash lotions and babycare products, of dermatologically satisfactory care products by improving the dermal and mucosal tolerability of the basic surfactants by combination with other mild surfactants and/or by additives.

Generally used in the cleaning of the human skin, the hair and the teeth are anionic surfactants such as, for example, soaps, alkyl sulfates, alkanesulfonates, fatty acid isethionates, α-olefinsulfonates, methyltaurides, sarcosides, acylglutamates and/or nonionic surfactants such as, for example, fatty alcohol polyglycol ethers and/or amphoteric surfactants such as alkylbetaines, alkylamidobetaines, imidazoline derivatives and cationic surfactants such as, for example, alkyltrimethylpentaoxyethylammonium lactate, which are employed alone or in combination with one another.

Some of these surfactants, especially alkyl sulfates, α-olefinsulfonates, alkylbetaines, alkylamidobetaines, are used to a large extent because of their very good foaming and cleansing action and their favorable prices. However, the disadvantage thereof is that they are relatively poorly tolerated by the skin and mucosa. This is because a particularly important criterion for the use of the surfactants for producing mild hair shampoos, shower products, intimate cleansers, classical soaps and so-called syndet soaps, as well as baby cleansing products, is the presence of very good mucosal tolerability.

It is also known to use protein/fatty acid condensates of low to moderate molecular mass, for example up to molecular mass 700. These protein/fatty acid condensates can be synthesized in a known manner by Schotten-Baumann acylation of protein hydrolysates with fatty acid chlorides or by condensation of the appropriate fatty acid methyl esters with protein hydrolysates. It is pointed out in the literature that these protein/fatty acid condensates of low to moderate molecular mass of about 500–700 have a good detergent action, which is said to decrease greatly with increasing molecular mass. On the other hand, the mucosal irritation is said to decrease only slightly with increasing molecular mass.

However, it has been found, surprisingly, that protein/fatty acid condensates with a higher molecular mass of, for example, 3,000–7,000 are far better tolerated by the skin and mucosa than are the corresponding protein/fatty acid condensates of low to moderate molecular mass. Moreover, the detergent and cleansing action is only inconsiderably less than that of the lower molecular weight protein/fatty acid condensates and is perfectly adequate for practical use.

The invention relates to high molecular weight protein/fatty acid condensation products obtained by reaction of one mole of a protein hydrolysate of average mclecular mass 3,000–7,000 with 0.5–3.0, preferably 2.0–2.5, moles of a $C_{12}$–$C_{18}$-fatty acid chloride in aqueous medium at a pH of 7 to 12.

The protein hydrolysates used as a basis are obtained in a customary way by hydrolysis of higher molecular weight protein products Particularly favorable protein hydrolysates are obtained from the connective tissues of mammals such as animal hides, bones, glues, chrome shavings and machine-cut glue stock. These products are hydrolyzed by a chemical or, preferably, by an enzymatic process to protein hydrolysates of the molecular mass indicated above. The stated values for the calculated average molecular masses were obtained from the molecular weight distribution by means of high-pressure liquid chromatography (HPLC) with the assistance of collagenous calibration peptides as a standard.

These protein hydrolysates are acylated by customary processes (Schotten-Baumann) with $C_{12}$–$C_{18}$-fatty acid chlorides in aqueous solution at a pH of 7–12, preferably 8–9.5. Aqueous solutions with a solids content of up to 60% by weight, preferably with a solids content of 30 to 40% by weight, are obtained. These aqueous solutions can be immediately processed further, but it is also possible for the protein/fatty acid condensation products to be isolated without difficulty from aqueous solutions as powders, for example by spray drying.

The protein/fatty acid condensation products obtained in this way surprisingly show no irritation whatever of the skin, eyes and mucosa, as is the case with protein/fatty acid condensation products which are based on protein hydrolysates with a molecular mass of 200–500.

The products according to the invention are non-toxic, non-sensitizing, non-irritant, exert an irritation-inhibiting effect in combination with conventional surfactants, show good compatibility with anionic and nonionic surfactants and, in some cases, also with quaternary ammonium compounds. They themselves display a mild cleansing action and are therefore very suitable as surfactant in washing and cleansing agents such as, for example, in shampoos, shower products, foam baths, syndet soaps, liquid soaps, household cleaners, rinses, dishwashing agents, detergents and protective soap pastes.

BRIEF DESCRIPTION OF THE DRAWING

In the accompanying Drawing.

FIG. 5 is a graphical plot illustrating the biodegradation behavior (measured in % dissolved organic carbon) over a thirty-day period of time for EFK 3000 compared to EFK 500 and an experimental control (sodium benzoate).

FIG. 6 is a bar graph illustrating skin test values (which values are considered to be correlated with skin irritation effects) for EFK 500, EFK 3000, and sodium lauryl sulfate.

FIG. 7 is a bar graph illustrating $D_{50}$ values (amount of tenside in ppm to cause albumin denaturation, a measure of dermal tolerability) for the tensides (surfactants) EFK 3000, EFK 500, and sodium laurylsulfate.

EXAMPLE 1

600 g of a 30% strength aqueous collagen hydrolysate solution with an average molecular mass of 3000 is adjusted to a pH of 9.5 with sodium hydroxide solution.

Then 63 g of 98% cocoyl chloride are introduced into this collagen hydrolysate solution. After the addition of the acid chloride is complete, the solution is heated to 50° C. and maintained at this temperature for 120 min.

The reaction mixture is then adjusted to a dry matter content of 35% with distilled water and brought to pH 6.5 with hydrochloric acid. It is possible after cooling to room temperature to add the preservatives and substances to improve the odor and improve the transparency. The product obtained in this way is called EFK 3000 hereinafter.

The high molecular weight protein/fatty acid condensates prepared as in Example 1 have, as the tables hereinafter show, a number of technical properties which make it possible to use them for producing cosmetic, pharmaceutical and industrial cleaning agents which are very well tolerated by the skin and mucosa.

EXAMPLE 2

1,400 g of a 50% strength aqueous collagen hydrolysate solution with an average molecular mass of 7,000 are adjusted to a pH of 11 with sodium hydroxide solution. 47.4 g of 98% pure cocoyl chloride are added dropwise to this solution while stirring vigorously. After the addition of the acid chloride is complete, the solution is heated to 60° C. and maintained at this temperature for 120 min.

The pH of the solution is then adjusted to 6.2 with hydrochloric acid and the dry matter content is adjusted to 30% with water.

The product is cooled to room temperature and then preservatives are added.

Surface tension

Figure 1:
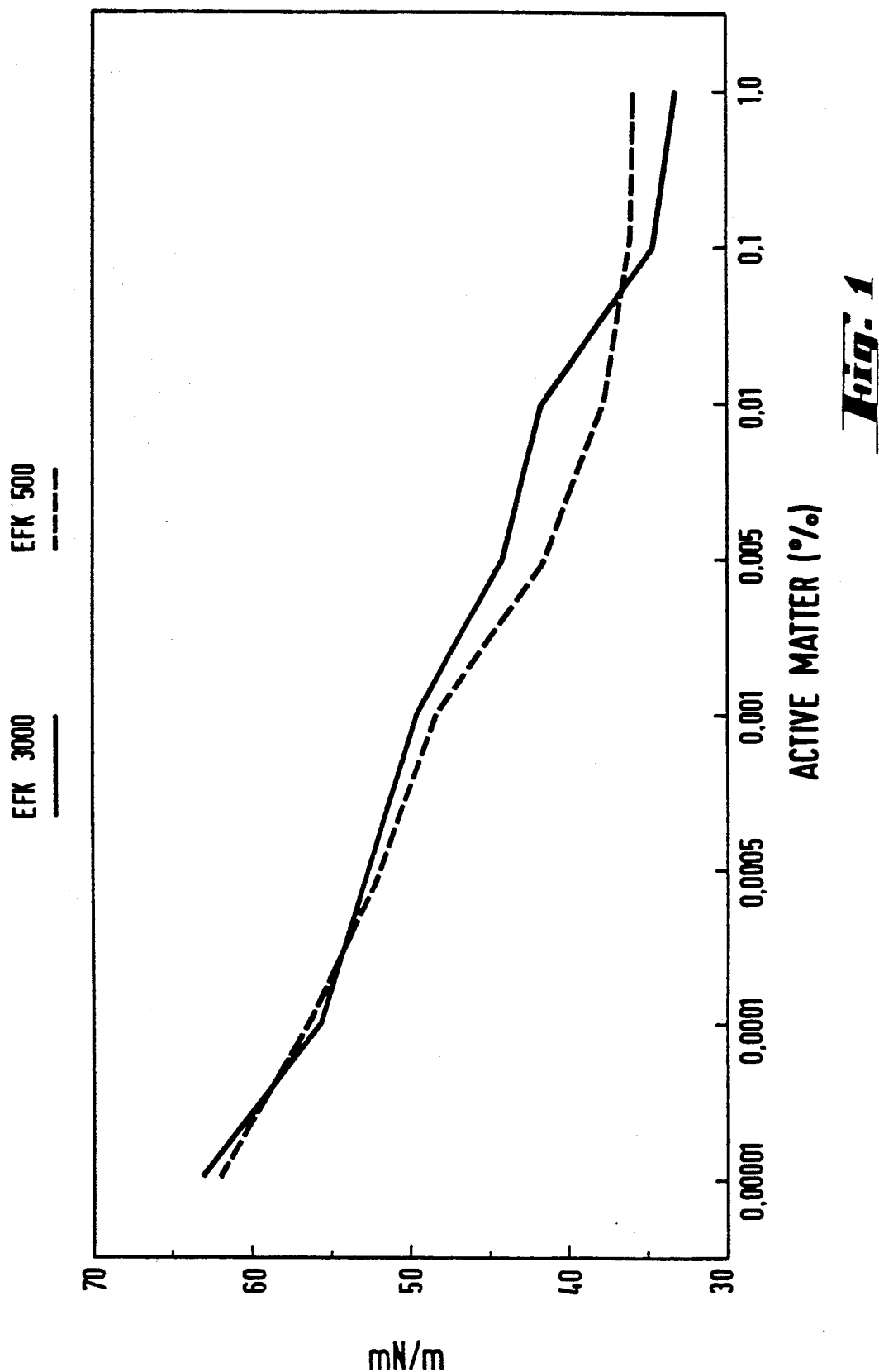
FIG. 1 is a graphical plot illustrating the decreasing surface tension values (in mN/m) obtained with increasing concentrations of active ingredient; a plot of the surface tension values of the condensation product of Example 1 (designated "EFK 3000") is compared with those of a comparison substance (designated "EFK 500").

The surface tension was determined by the ring-detachment method with a digital tensiometer (Krüss, K 10 ST) in distilled water at 20° C. The substance prepared as in Example 1 was used for the determination. The values are shown in FIG. 1, where the substance according to the invention has been called EFK 3000. The comparison substance, called EFK 500, is a protein/fatty acid condensate according to the state of the art with an average molecular mass of 500. It is evident that even the higher molecular weight EFK 3000 shows the decrease in surface tension which is desired in practice.

Ross-Miles foaming behavior

Figure 2:
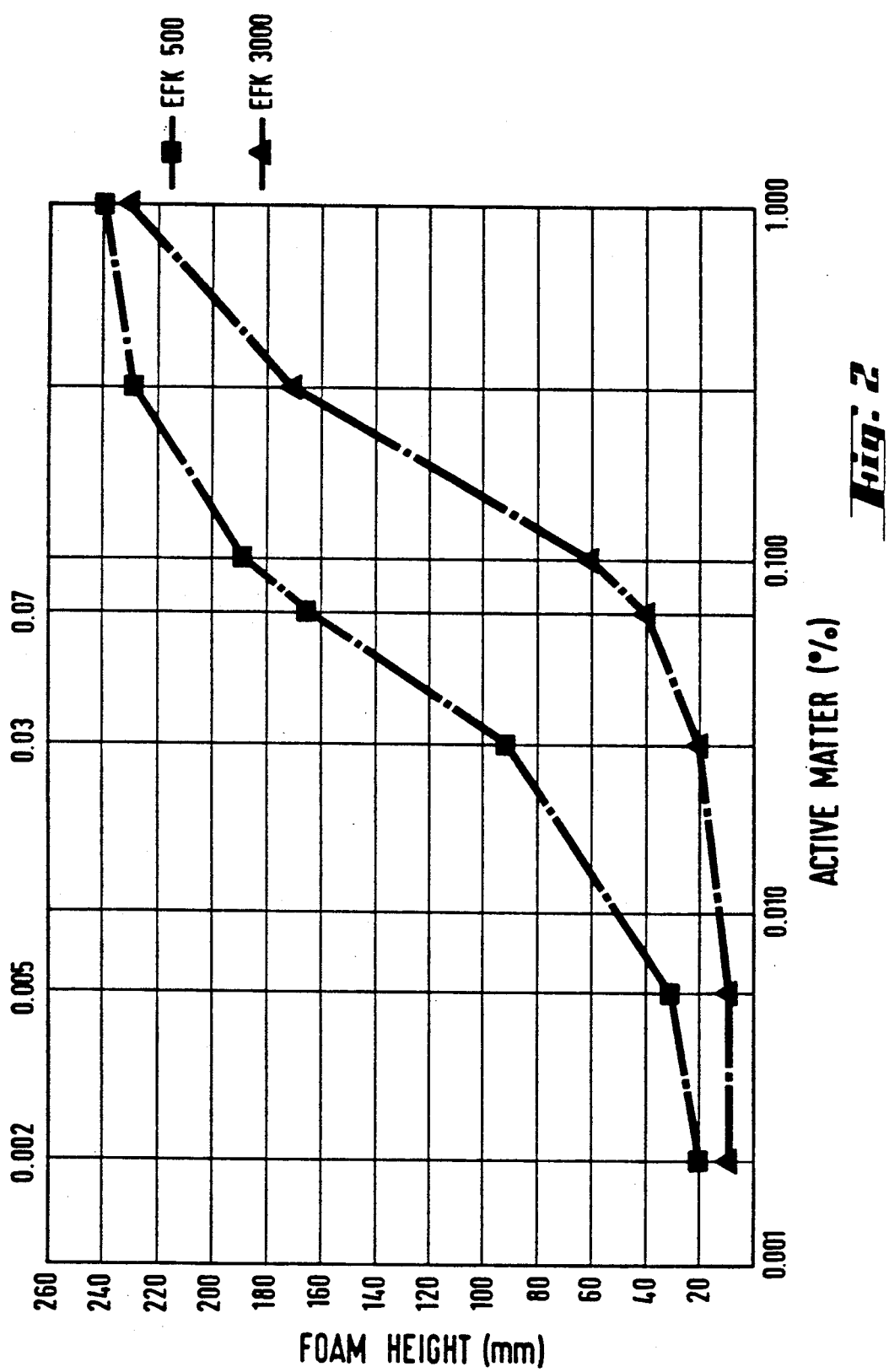
FIG. 2 is a graphical plot illustrating the increasing Ross-Miles foam height values obtained with increasing active ingredient concentrations; as in FIG. 1, a comparison is made between the values for EFK 3000 and the values for EFK 500.

The foaming behavior of EFK 3000 according to Example 1 was tested by a method based on that of Ross-Miles. The foam curve is depicted in FIG. 2. The foaming behavior is good in the concentrations between 0.5 and 1% which are customary in practice; particular attention is drawn to the generally desired small bubbles in the foam and the stability with time which is associated therewith.

Stability

For practical use, surfactants are required to be stable to UV light and elevated temperatures, for example +40° C., and to be pH-resistant. As Table 1 hereinafter shows, EFK 3000 according to Example 1 has both good color stability and very good pH stability after storage at room temperature and +40° C. for 6 months.

TABLE 1

| EFK 3000 stability test | | | |
|---|---|---|---|
| Color stability | Dark | 40° C. | Light |
| Iodine color number at start of test | 8 | 8 | 8 |
| Iodine color number after 2 months | 8 | 8 | 8 |
| Iodine color number after 6 months | 8 | 9 | 8 |
| pH stability | | +20° C. | +40° C. |
| pH (10% strength) at start of test | | 7.44 | 7.44 |
| pH (10% strength) after 2 months | | 7.28 | 7.26 |
| pH (10% strength) after 6 months | | 7.28 | 7.26 |

Cleansing power

The cleansing power was tested on soiled cotton fabric on the one hand, and on the human skin on the other.

| Pigment cleansing power<br>The detergent action was determined on fabric using a<br>Launder-Ometer under the following conditions.<br>Cotton fabric soiled with sebum/pigment. | |
|---|---|
| Washing temperature | 30° C. |
| Washing time | 5 min |
| Concentration | 10 g/l |
| Water hardness | 15° German hardness |
| pH | 6.5. |

Figure 3:
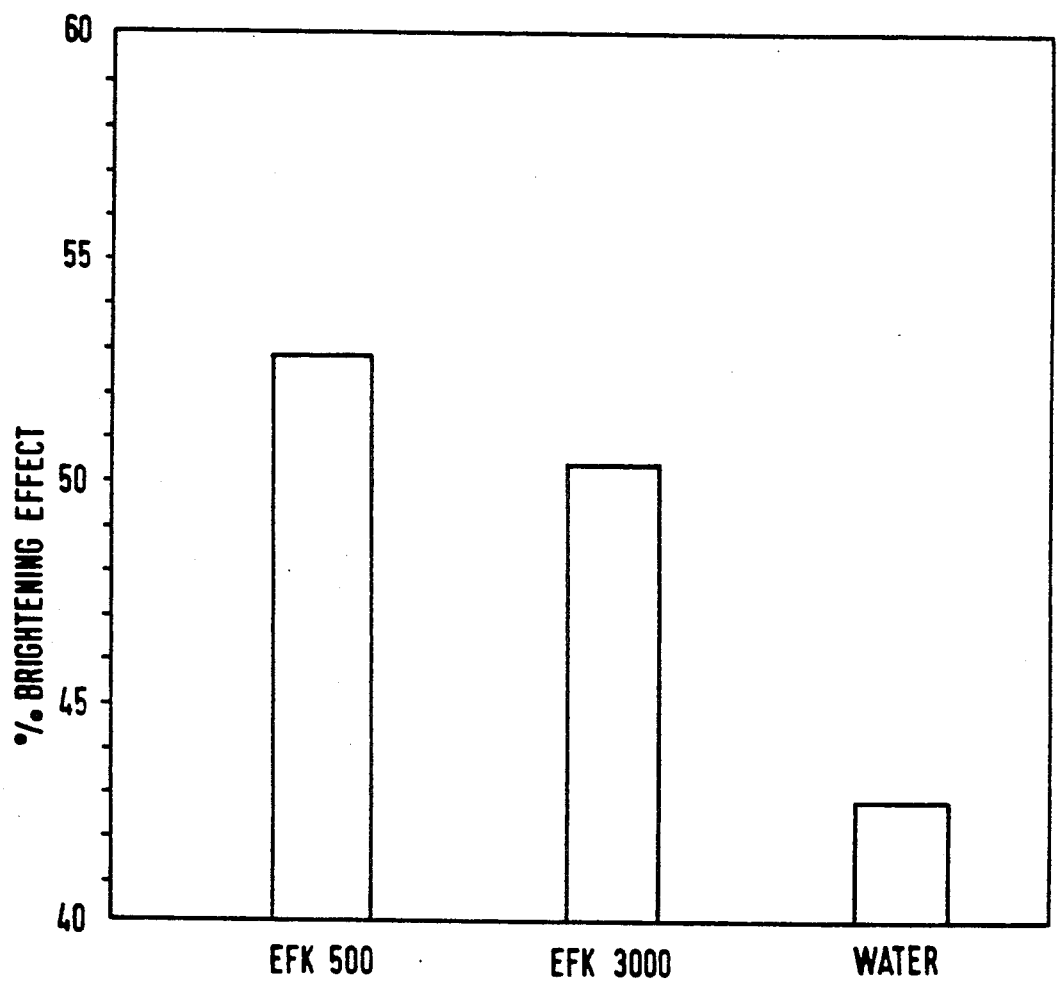
FIG. 3 is a bar graph illustrating the degree of soil removal (as measured by "% brightening" using a Launder-Ometer), i.e. the detergent action, of EFK 500, EFK 3000 and pure water.

FIG. 3 makes it clear that the detergent action of EFK 3000 is still adequate for use in cleansing agents and is only slightly below the value for the low molecular weight EFK 500.

Cleansing effect on the human skin

The determination of the washing effect using a Tronnier skin washing machine operates with a very particular model soil which contains fat- and water-soluble substances as well as pigments in order to detect the totality of the surfactant effect.

Figure 4:
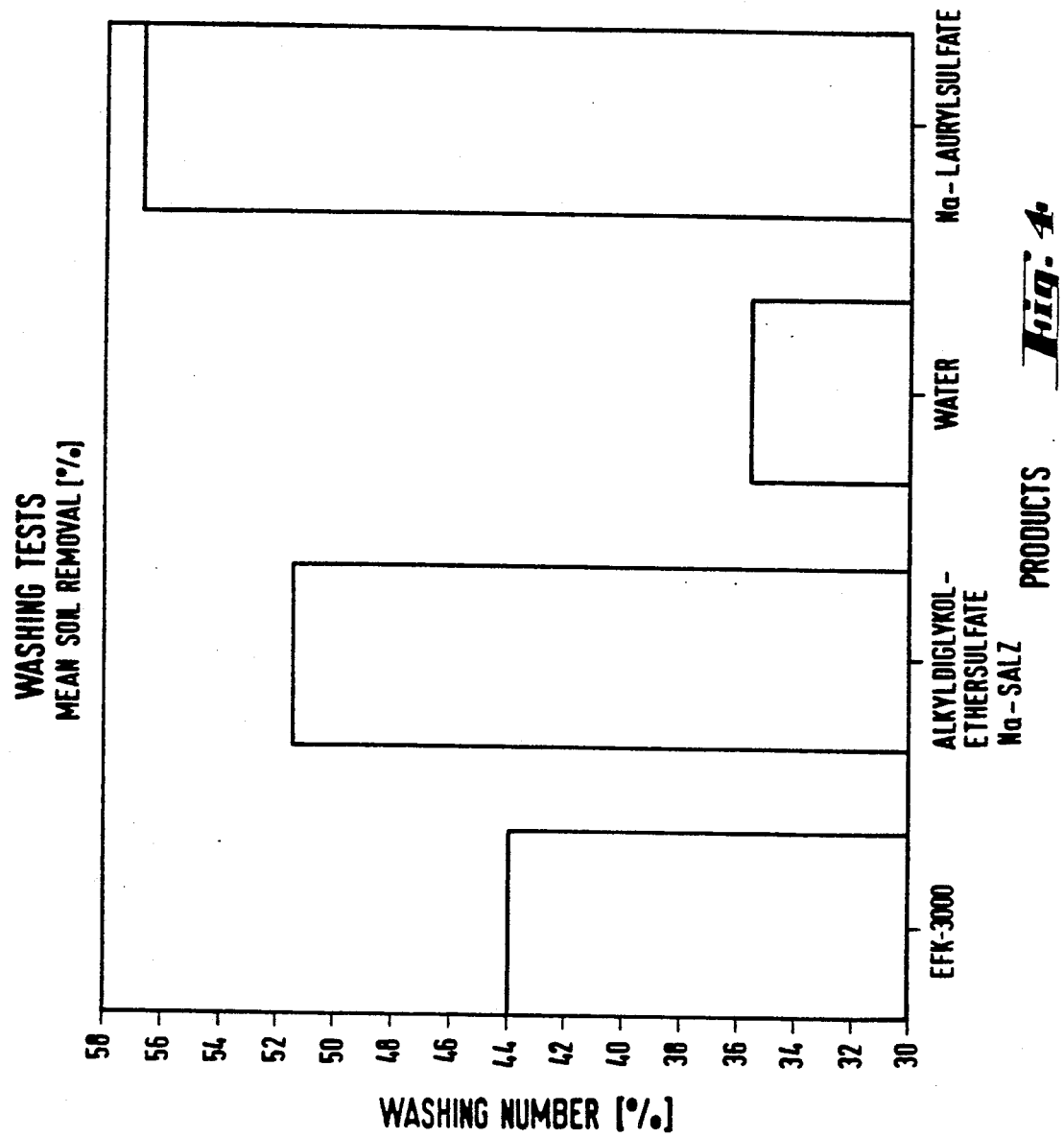
FIG. 4 is a bar graph illustrating "washing number" values (washing effect minus soil effect) for EFK 3000, alkyl diglycolether sulfate sodium salt, pure water, and sodium laurylsulfate.

FIG. 4 makes it clear that the cleansing power of EFK 3000 is satisfactory by comparison with the surfactants in Na lauryl sulfate and alkyldiglycol ether sulfate Na salt, as well as pure water (the washing number is defined as the washing effect minus the soil effect).

Biodegradation

The biodegradation was determined using the modified OECD screening test 301 E, in which the rate of biodegradation of the test substance is followed analytically (reduction in DOC=dissolved organic carbon). The degradation curves in FIG. 5 show that EFK 3000 can be degraded considerably more rapidly than the corresponding low molecular weight EFK 500. After a test period of only 5 days EFK 3000 reaches the 60% total degradation=mineralization to carbon dioxide and water, which is the value specified by statute for the future.

Zein test

The zein test (protein from corn grain) supplies reliable information on the degreasing and skin-irritant properties of surfactants. There is a relation between the dermal tolerability of surfactants and the solubilization of zein, according to which surfactants with high zein values are more strongly degreasing and skinirritant and thus exert a more powerful effect on skin roughness. A connection with the critical micelle concentration of the surfactants is also described in the literature. Surfactants with high CMC values also have high zein values and, moreover, show the greatest irritant effect in the Duhring chamber test.

This in vitro test shows, for example as in FIG. 6, that sodium lauryl sulfate, which is generally regarded as aggressive, yields a very high value while EFK 3000 shows no zein solubility, also in comparison with EFK 500.

Albumin denaturation test

The albumin denaturation test is likewise a criterion for characterizing the dermal tolerability of surfactants. The results of this test show a good correlation with the results of measurements of skin roughness (methylene blue method, image analysis). The higher the $D_{50}$ value the lower is the protein-damaging effect of the product and, according to Frosch, the more favorable are the dermatological properties in vivo. FIG. 7 shows the great superiority of the high molecular weight protein surfactant EFK 3000 by comparison with the product EFK 500. EFK 3000 is outside the range of the test method, i.e. no denaturation of albumin is detectable even with higher addition of EFK 3000. The standard substance sodium lauryl sulfate shows a great protein-damaging effect.

Acute oral toxicity on rats

The $LD_{50}$ value was determined in rats in a known manner.

The value for EFK 3000 was above 46.4 ml/kg of body weight on oral intake and is thus a multiple of that for most surfactants, for which the value is between 1 and 2 ml/kg. It was not possible to calculate the $LD_{50}$ because no animal died at the highest reasonable dose of 46.4 ml/kg.

Primary dermal irritation on rabbits

The primary dermal irritation on rabbits is used to determine the acute toxicity. As shown in the table below, testing the substance in a concentration of 32% active compound revealed no irritant properties; by contrast, EFK 500, which was tested as comparison product, still showed a slight irritant effect.

TABLE 2

Primary dermal irritation on rabbits
Method: FDA § 1500.41
Acute toxicity

| Dermal irritation index | 100% commercial concentration (32% detergent) EFK 3000 |
|---|---|
| Shaven intact skin | 0 |
| Shaven scarified skin | 0.1 |

TABLE 2-continued

Primary dermal irritation on rabbits
Method: FDA § 1500.41
Acute toxicity

| Total irritation index | 0.1 |
|---|---|
| Evaluation | No irritant properties |
| Total irritation index | Evaluation |
| 0.0–0.5 | non-irritant |
| 0.6–3.0 | slightly irritant |
| 3.1–5.0 | moderately irritant |
| 5.1–8.0 | extremely irritant |

Irritation of the rabbit eye by the Draize method

Testing the irritation of the rabbit eye by the EFK 3000 according to the invention revealed no irritation whatever even at the high detergent concentration of 33%, although the Draize assessment of the cornea, iris and conjunctiva was carried out only 5 min after application (Tab. 3). When classifying the mucosal tolerability of most surfactants, the first assessment of the score does not take place until after 24 h, during which period it is of course possible for a large fraction of the reversible damage (such as, for example, slight opacity, swelling, discharge) to have disappeared again. Draize testing of the low molecular weight EFK 500 revealed a total irritation index above 12.49, although the first assessment was not carried out until after 24 h. The product EFK 3000 behaves like the control substance, physiological saline.

TABLE 3

Irritation of the rabbit eye (Draize test)
Method: FDA § 1500.42

| Irritation index | 100% commercial concentration (32% detergent) EFK 3000 |
|---|---|
| 5 minutes | 0 |
| 15 minutes | 0 |
| 30 minutes | 0 |
| 1 hour | 0 |
| 2 hours | 0 |
| 4 hours | 0 |
| 24 hours | 0 |
| 48 hours | 0 |
| 72 hours | 0 |

Total irritation index

The high molecular weight protein/fatty acid condensation products with a molecular mass between 3,000 and 7,000 can be used in a known manner for producing cosmetic, pharmaceutical and industrial cleaning agents which are very well tolerated by the skin and mucosa. They can be employed both alone and in combination with the known anionic, nonionic, cationic and amphoteric surfactants in the customary mixing ratios for producing these products.

The examples which follow are intended to illustrate the possible uses of the high molecular weight protein/fatty acid condensates but without restricting them thereto.

Example 1
Hair shampoo

| Protein/fatty acid condensate of average molecular mass 3,000, according to Example 1 (EFK 3000) | 7.0% |
|---|---|
| Alkyldiglycol ether sulfate sodium salt | 45.0% |

|  |  |
|---|---|
| (28% strength) | |
| Perfume oil | 0.3% |
| Sodium chloride | 3.1% |
| Preservatives, perfume oil, colorants and water | ad 100.0% |
| Example 2 | |
| Baby shampoo | |
| EFK 3000 | 28.0% |
| Alkyldiglycol ether sulfate sodium salt (28% strength) | 7.0% |
| Alkylamidopropylbetaine | 5.0% |
| Example 3 | |
| Shower product | |
| EFK 3000 | 5.0% |
| Alkyltriglycol ether sulfate sodium salt (28% strength) | 39.0% |
| Alkylamidobetaine | 9.0% |
| Sodium chloride | 1.0% |
| Water, preservative, perfume oil | ad 100.0% |
| Example 4 | |
| Intimate cleanser | |
| EFK 3000 | 8.0% |
| Amide ether sulfate sodium salt | 5.0% |
| Alkylamidobetaine | 3.0% |
| Water, active compounds, preservative, perfume oil | ad 100.0% |
| Example 5 | |
| Facial cleanser | |
| EFK 3000 | 4.0% |
| Acylglutamate monosodium salt | 2.0% |
| Lauroylsarcoside sodium salt | 4.0% |
| Water, perfume oil, preservative, consistency regulator | ad 100.0% |
| Example 6 | |
| Hand cleanser | |
| EFK 3000 | 2.0% |
| Sodium alkyl sulfate | 4.0% |
| α-Olefinsulfonate | 5.0% |
| Secondary alkanesulfonate sodium salt | 2.0% |
| Water, preservative, perfume oil | ad 100.0% |
| Example 7 | |
| Hand cleanser with disinfectant action | |
| EFK 3000 | 3.0% |
| Secondary alkanesulfonate sodium salt | 10.0% |
| Substance with disinfectant action | 0.2% |
| Water, preservative, perfume oil | ad 100.0% |
| Example 8 | |
| Manual dishwashing agent | |
| EFK 3000 | 10.0% |
| Secondary alkanesulfonate sodium salt (60% strength) | 30.0% |
| Alkyldiglycol ether sulfate sodium salt (29% strength) | 10.0% |
| Water, preservative, solubilizer, perfume oil | ad 100.0% |

We claim:

1. A high molecular weight protein/fatty acid condensation product obtained by the reaction of the components comprising a protein hydrolyzate of average molecular mass 3,000 to 7,000, said protein hydrolyzate consisting essentially of a collagen hydrolyzate produced by enzymatic hydrolysis of an essentially collagen product of higher molecular weight relative to said average molecular mass, with 0.5 to 3 moles, per mole of said protein hydrolyzate, of a $C_{12}$–$C_{18}$ fatty acid chloride, in aqueous medium at a pH of 7 to 12.

2. A protein/fatty acid condensation product as claimed in claim 1, obtained by a said reaction in which the amount of $C_{12}$–$C_{18}$ fatty acid chloride is 2 to 2.5 moles per mole of said protein hydrolyzate.

3. A protein fatty acid condensation product as claimed in claim 1, obtained by a said reaction in which the aqueous medium is at a pH of 8 to 9.5.

4. An aqueous composition comprising an effective amount, up to 60% by weight, of the protein/fatty acid condensation product of claim 1.

5. A powdered composition comprising a protein/fatty acid condensation product of claim 1 which has been spray-dried.

6. A surfactant composition comprising an effective amount of the protein/fatty acid condensation product of claim 1.

7. A method of cleansing comprising the step of applying the surfactant composition of claim 6 to the material to be cleansed.

* * * * *